(12) United States Patent
Tabata et al.

(10) Patent No.: US 10,196,584 B2
(45) Date of Patent: Feb. 5, 2019

(54) PRODUCTION METHOD OF HIGHLY UNSATURATED FATTY ACID WITH HIGH PURITY/HIGH YIELD

(71) Applicant: Bizen Chemical Co., Ltd., Akaiwa-shi, Okayama (JP)

(72) Inventors: Hiroshi Tabata, Akaiwa (JP); Tetsuro Taira, Akaiwa (JP); Jun Fujii, Akaiwa (JP); Yoshihisa Misawa, Akaiwa (JP); Yoshio Shimizu, Akaiwa (JP)

(73) Assignee: Bizen Chemical Co., Ltd., Akaiwa-shi, Okayama (JP)

( * ) Notice: Subject to any disclaimer, the term of this patent is extended or adjusted under 35 U.S.C. 154(b) by 0 days.

(21) Appl. No.: 15/577,294

(22) PCT Filed: May 30, 2016

(86) PCT No.: PCT/JP2016/002612
§ 371 (c)(1),
(2) Date: Nov. 27, 2017

(87) PCT Pub. No.: WO2016/194359
PCT Pub. Date: Dec. 8, 2016

(65) Prior Publication Data
US 2018/0148664 A1    May 31, 2018

(30) Foreign Application Priority Data

Jun. 1, 2015  (JP) .................................. 2015-111798

(51) Int. Cl.
*C11B 3/02*      (2006.01)
*C07C 67/60*   (2006.01)
(Continued)

(52) U.S. Cl.
CPC ................ *C11B 3/02* (2013.01); *C07C 67/58* (2013.01); *C07C 67/60* (2013.01); *C07C 67/62* (2013.01); *C07C 69/587* (2013.01); *C07C 51/487* (2013.01)

(58) Field of Classification Search
CPC . C11B 3/02; C11B 3/06; C11B 7/0008; C11C 1/005; C07C 67/58; C07C 67/60; C07C 51/487; C07C 57/03; C07C 69/587
See application file for complete search history.

(56) References Cited

U.S. PATENT DOCUMENTS 5,189,189 A *   2/1993  Misawa ................ C07C 51/487
                                                             554/194
8,680,305 B2 *  3/2014  Sakaguchi .............. C07C 67/58
                                                             554/175

FOREIGN PATENT DOCUMENTS

EP           0576191 A2    12/1993
JP           3001954 B2      1/1991
(Continued)

OTHER PUBLICATIONS

JP 2001240893, Kobayashi, H. et al., Purification of eicosapentaenoic acid or is derivative used in drug, involves forming silver nitrate complex of natural fatty acid mixtures of preset ratio of specific fatty acids and eicosapentaenoic acid, English translation, 22 pages (Year: 2001).*

(Continued)

*Primary Examiner* — Yate' K Cutliff
(74) *Attorney, Agent, or Firm* — Seed IP Law Group LLP

(57) ABSTRACT

A production method of highly unsaturated fatty acids with a high purity/high yield that compensates for shortcomings of conventional techniques is provided.
A purification method of highly unsaturated fatty acids and/or derivatives thereof comprising (a) contacting and stirring first raw materials comprising the substances with a (Continued)

first silver salt aqueous solution to collect a first oil layer and a first aqueous layer; (b) separating the first aqueous layer into a second silver salt aqueous solution and the substances; and (c) contacting and stirring the first oil layer with the second silver salt aqueous solution for separation into an oil layer and an aqueous layer to obtain a second aqueous layer comprising the substances.

15 Claims, 4 Drawing Sheets

(51) Int. Cl.
*C07C 67/58* (2006.01)
*C07C 67/62* (2006.01)
*C07C 69/587* (2006.01)
*C07C 51/487* (2006.01)

(56) References Cited

FOREIGN PATENT DOCUMENTS

| JP | 6-49480 A | | 2/1994 | |
|----|-----------|---|--------|---|
| JP | 2786748 B2 | | 8/1998 | |
| JP | 2895258 B2 | | 5/1999 | |
| JP | 2935555 B2 | | 8/1999 | |
| JP | 2001240893 | * | 9/2001 | ............... C11C 1/08 |
| JP | 2001335794 | * | 12/2001 | ............. C11C 1/008 |
| JP | 2015-091940 A | | 5/2015 | |

OTHER PUBLICATIONS

JP 2001335794, Kobayashi, H, et al., Purification of docosahexaenoic acid for pharmaceutical use comprising mixing unsaturated fatty acid comprising DHA and aqueous silver nitrate at specific mixing rate and dissociating formed complex with water, English translation, 15 pages (Year: 2001).*

* cited by examiner

PRODUCTION METHOD OF HIGHLY UNSATURATED FATTY ACID WITH HIGH PURITY/HIGH YIELD

TECHNICAL FIELD

The present invention relates to a novel production method of a highly unsaturated fatty acid ethyl ester. The present invention also relates to a purification method of a highly unsaturated fatty acid ethyl ester.

The present invention particularly relates to a purification technique from highly unsaturated fatty acids derived from animals and plants, and microorganism fats and oils such as fish oils, extracted oils of algae, and extracted oils from genetically engineered plants; and derivatives thereof, and particularly to a method of industrially and cheaply producing pharmaceutical-grade products.

BACKGROUND ART

In recent years, unsaturated fatty acids are noticed not only as essential fatty acids in supplements, but since particularly eicosapentaenoic acid ethyl ester was approved as a therapeutic drug of arteriosclerosis obliterans and hyperlipidemia as switch OTC, there is an expanding market for pharmaceutical-grade EPA ethyl. In other words, highly unsaturated fatty acids have been utilized in pharmaceutical products and health foods. However, since highly unsaturated fatty acids have many double bonds, it is difficult to obtain them with chemical synthesis.

Highly unsaturated fatty acids are produced by extraction and purification from marine organisms such as fish oils. However, contents of highly unsaturated fatty acids are small, and thus a purification technique with a high yield/high purity has been desired.

Conventionally, with regard to methods of separating a specific fatty acid from a mixture of fatty acids or monoesters, there were mainly distillation, molecular sieve, and supercritical fluid extraction as separation methods using the difference in carbon numbers; and low-temperature fractionation, urea addition, silver complex formation, solvent fractionation, and column chromatographic methods using silver ion treatment resin and ODS, as separation methods using the number of double bonds. Although these purification methods are simple, each of them have shortcomings such as insufficiency in separation, and unsuitableness for industrial mass treatment even if high purification is possible, as in the case of chromatographic methods. In actual industrial production, highly pure fatty acids are produced by combining a plurality of these purification methods. However, there are many points to be improved in the complication of the purification methods and in the purity/yield.

The principle of silver nitrate treatment lies on the point that, among highly unsaturated fatty acids, particularly highly unsaturated fatty acids having a large number of double bonds within the molecule form a complex of the double bonds within the molecule and silver ions, by mixture with a silver nitrate aqueous solution. By utilizing this property, analysis on unsaturated fatty acids that utilizes the difference of holding force from a silica gel column carrier carrying silver ions, has been practiced. In the industrial production method of highly unsaturated fatty acids, water solubility of this complex is utilized to fractionate fat-soluble fractions, which include saturated fatty acids or moderately/highly unsaturated fatty acids having a small number of double bonds within the molecule, as oil layers.

Since a water-soluble complex can be separated into silver nitrate and purified highly unsaturated fatty acids by heating the solution, such simple process enables purification of highly unsaturated fatty acids in an industrial scale.

However, silver nitrate treatment has drawbacks as a production method in that the price of silver nitrate, which is the raw material, is high, and there are big fluctuations in the price. In addition, since not all of the targeted highly unsaturated fatty acids form a complex, and some of them will remain in the oil layer, it is difficult to say that this is a production method achieving a high yield. As a result, there is a drawback that the production cost is raised.

Furthermore, in principle, there is a difficulty in completely removing highly unsaturated fatty acids having three or more double bonds within the molecule as impurities, in silver nitrate treatment. At the time of high-purity purification achieving pharmaceutical grades, such impurities become the cause of reducing the yield of purification methods in the preceding purification steps and the subsequent purification steps.

Representative purification methods in conventional techniques will be exemplified below.

Problems of techniques that have been used in purification of unsaturated fatty acids and derivatives thereof will be described below.

1) Precision Distillation
Characteristic: a method of separation by utilizing differences in boiling points of each component.
Problem: thermal denaturation may occur; a long time is required in purification of highly pure products.
2) Molecular Distillation
Characteristic: little thermal influence at the time of distillation.
Problem: low separation ability.
3) Urea Treatment Method
Characteristic: utilizing the property of dissolved urea, i.e., incorporating in coexisting linear molecules while forming hexagonal columnar adduct crystals at the time of crystallization.
Problem: low selectivity; waste disposal due to derivation of urea adduct.
4) Silver Nitrate Treatment
Characteristic: utilizing the property of a silver nitrate aqueous solution, i.e., forming a complex with double bonds of fatty acids.
Problem: the price of silver is unstable; involve impurities.
5) Fixed-Bed Chromatography
Characteristic: small thermal influence; separation with high precision is enabled.
Problem: large usage of eluents; unsuitable for industrial production.
6) Simulated Moving-Bed Chromatography
Characteristic: suitable for industrialization due to small usage of eluents and continuous operations.
Problem: ODS fillers, which are often used for separation of unsaturated fatty acids, are expensive; since only single solvent can be used, gradient separation is not possible.

With regard to purification techniques of eicosapentaenoic acid (EPA) ethyl esters, for example, Patent Literatures 1-4 describe silver nitrate treatment as an industrially remarkable purification technique of unsaturated fatty acids and derivatives thereof. However, the methods of Patents 1-4 have problems as follows:

1) unsaturated fatty acids other than EPA and docosahexaenoic acid (DHA) also form a complex at the same time, and it is difficult to obtain highly unsaturated fatty acids with high purity; and 2) some of highly unsaturated fatty acids do not form a complex, and the yield is reduced by disposing them.

A production method of highly unsaturated fatty acids with a high purity/high yield that compensates for the shortcomings of the conventional techniques is required.

CITATION LIST

Patent Literature

[PTL 1]
Japanese Patent No. 3001954
[PTL 2]
Japanese Patent No. 2786748
[PTL 3]
Japanese Patent No. 2935555
[PTL 4]
Japanese Patent No. 2895258

SUMMARY OF INVENTION

Technical Problem

The present invention solves the above-described problems regarding purification of highly unsaturated fatty acids and derivatives thereof.

Solution to Problem

One aspect of the present invention is characterized with a purification method of highly unsaturated fatty acids and derivatives thereof using a silver salt aqueous solution, wherein: highly unsaturated fatty acids and derivatives thereof, which are raw materials, are added to a solution where a complex is formed with highly unsaturated fatty acids and derivatives thereof in an oil layer created as a by-product and a silver salt aqueous solution to collect the highly unsaturated fatty acids and derivatives thereof in the oil layer; and the production cost is reduced by improving the yield.

In order to obtain highly pure fat-soluble substances of pharmaceutical grades, it is deficient to only perform purification with a silver salt aqueous solution as in the conventional technique, and there is a need to combine other purification methods. In another aspect of the present invention, high purification is achieved by reducing arachidonic acid, eicosatetraenoic acid, and derivatives thereof, which are difficult to be removed at the time of purification, than the conventional methods. In other words, in the another aspect of the present invention, the targeted fat-soluble substances can be obtained at a high yield.

A further aspect of the present invention is characterized in that the method of the present invention can be used to purify highly unsaturated fatty acids and derivatives thereof up to pharmaceutical grades at a lower cost than the conventional purification method using a silver salt aqueous solution.

In another aspect of the present invention, a mixture of highly unsaturated fatty acids and derivatives thereof, which are raw materials, is mixed with a silver salt aqueous solution to form a water-soluble complex of specific highly unsaturated fatty acids and the silver salt, and the specific highly unsaturated fatty acids are once purified from this aqueous layer. In a specific aspect of the present invention, a solution of silver salt is added again to an oil layer created as a by-product at the time of purification to allow complex formation with silver nitrate, and then the raw materials are further added to obtain the specific highly unsaturated fatty acids and derivatives thereof with a high purity/high yield, thereby achieving reduction of production cost.

In other words, the present invention provides, for example, a method comprising:
i) performing complex formation with raw materials in a state where a complex of highly unsaturated fatty acids in an oil layer created as a by-product and silver salt is formed; and
ii) forming a complex of the oil layer and silver salt, thereby performing the method of (1) in Item A1 described below.

For example, the present invention provides the following.
(Item A1)
A method of reducing the production cost of fat-soluble substances by achieving a high yield at the time of highly-pure purification of the fat-soluble substances, comprising:
(1) forming a complex at a low temperature with a silver salt aqueous solution and a mixture comprising highly unsaturated fatty acids and derivatives thereof, which are raw materials, and after collection as an aqueous solution, obtaining purified highly unsaturated fatty acids and derivatives thereof by separation from the complex using heating, solvent extraction, and the like;
(2) after separation of an oil layer, adding a silver salt aqueous solution to the oil layer created as a by-product at that time to form a complex again at a low temperature; after separating an oil layer, further adding raw materials to form a complex at a low temperature; and after collection as an aqueous solution, obtaining purified highly unsaturated fatty acids and derivatives thereof by separation from the complex using heating, solvent extraction, and the like; and
(3) performing treatment on the oil layer created as a by-product at the time of the above-described step (2) in the same manner as the above-described step (2), and repeating such treatment in the next batch and onwards, thereby collecting highly unsaturated fatty acids and derivatives thereof in the oil layer.
(Item A2)
The method according to item A1, wherein contamination of arachidonic acid and eicosatetraenoic acid is prevented, and a high purity is achieved, as compared to a conventional method using a silver salt aqueous solution.
(Item A3)
The method according to item A1, wherein precision distillation, molecular distillation, chromatographic method, or urea addition method is combined as a pretreatment or posttreatment with the present invention to achieve a high yield production method, upon high-purity (purity of 97% or higher) purification of fat-soluble substances of pharmaceutical grades.
(Item A4)
The method according to item A1, wherein the fat-soluble substances are selected from the group consisting of docosapentaenoic acid, eicosapentaenoic acid, docosahexaenoic acid, and lower alcohol esters of those, having five or more double bonds within the molecule.

The present invention provides, for example, the following first exemplary embodiment (see FIG. 1):
(Item 1)
A purification method of substances selected from the group consisting of highly unsaturated fatty acids and derivatives thereof, the method comprising:

(a) contacting and stirring first raw materials comprising the substances with a first silver salt aqueous solution to collect a first oil layer and a first aqueous layer;
(b) separating the first aqueous layer into a second silver salt aqueous solution and the substances; and
(c) contacting and stirring the first oil layer with the second silver salt aqueous solution for separation into an oil layer and an aqueous layer to obtain a second aqueous layer comprising the substances.

(Item 2)
A purification method of substances selected from the group consisting of highly unsaturated fatty acids and derivatives thereof, the method comprising:
(a) contacting and stirring first raw materials comprising the substances with a first silver salt aqueous solution to collect a first oil layer and a first aqueous layer;
(b) separating the first aqueous layer into a second silver salt aqueous solution and the substances; and
(c) contacting and stirring the first oil layer with the first silver salt aqueous solution for separation into an oil layer and an aqueous layer to obtain a second aqueous layer comprising the substances.

(Item 3)
The method according to item 1 or 2, further comprising
(d) contacting and stirring the second aqueous layer with second raw materials comprising the substances to collect a second oil layer and a third aqueous layer, wherein the second oil layer comprises the substances.

(Item 4)
The method according to item 3, further comprising
(e) separating the third aqueous layer into a third silver salt aqueous solution and the substances.

(Item 5)
The method according to item 3, further comprising
(f) separating the substances from the second oil layer.

(Item 6)
The method according to item 4, further comprising
(g) contacting and stirring a silver salt aqueous solution selected from the group consisting of the first silver salt aqueous solution, the second silver salt aqueous solution, and the third silver salt aqueous solution, with the second oil layer for separation into an oil layer and an aqueous layer to obtain a fourth aqueous layer comprising the substances.

(Item 7)
The method according to any one of items 1 to 6, wherein the highly unsaturated fatty acid derivatives are highly unsaturated fatty acid ethyl esters.

(Item 8)
The method according to item 7, wherein the highly unsaturated fatty acid ethyl esters are selected from the group consisting of docosapentaenoic acid, eicosapentaenoic acid, docosahexaenoic acid, and ethyl esters of lower alcohols of those, having five or more double bonds within the molecule.

(Item 9)
The method according to any one of items 1 to 8, wherein the silver salt aqueous solution is a silver nitrate aqueous solution.

(Item 10)
A purification method of substances selected from the group consisting of highly unsaturated fatty acids and derivatives thereof, comprising contacting and stirring:
(i) a first oil layer collected by contacting and stirring first raw materials comprising the substances with a first silver salt aqueous solution; with (ii) a second silver salt aqueous solution obtained by separating a first aqueous layer collected by contacting and stirring the first raw materials comprising the substances with the first silver salt aqueous solution, into the second silver salt aqueous solution and the substances,
for separation into an oil layer and an aqueous layer to collect a second aqueous layer comprising the substances.

(Item 11)
A purification method of substances selected from the group consisting of highly unsaturated fatty acids and derivatives thereof, the method comprising contacting and stirring (i) a first oil layer collected by contacting and stirring first raw materials comprising the substances with a first silver salt aqueous solution, with (ii) the first silver salt aqueous solution, for separation into an oil layer and an aqueous layer to collect a second aqueous layer comprising the substances.

(Item 12)
The method according to item 10 or 11, further comprising
(b) contacting and stirring the second aqueous layer with second raw materials comprising the substances to collect a second oil layer and a third aqueous layer, wherein the second oil layer comprises the substances.

(Item 13)
The method according to item 12, further comprising
(c) separating the third aqueous layer into a third silver salt aqueous solution and the substances.

(Item 14)
The method according to item 12, further comprising
(d) separating the substances from the second oil layer.

(Item 15)
The method according to item 12 or 13, further comprising
(e) contacting and stirring a silver salt aqueous solution selected from the group consisting of the first silver salt aqueous solution, the second silver salt aqueous solution, and the third silver salt aqueous solution with the second oil layer, for separation into an oil layer and an aqueous layer to obtain a fourth aqueous layer comprising the substances.

(Item 16)
The method according to any one of items 10 to 15, wherein the highly unsaturated fatty acid derivatives are highly unsaturated fatty acid ethyl esters.

(Item 17)
The method according to item 16, wherein the highly unsaturated fatty acid ethyl esters are selected from the group consisting of docosapentaenoic acid, eicosapentaenoic acid, docosahexaenoic acid, and ethyl esters of lower alcohols of those, having five or more double bonds within the molecule.

(Item 18)
The method according to any one of items 10 to 17, wherein the silver salt aqueous solution is a silver nitrate aqueous solution.

The present invention provides, for example, the following second exemplary embodiment (see FIGS. 2-4):

(Item B1)
A purification method of substances selected from the group consisting of highly unsaturated fatty acids and derivatives thereof, the method comprising not less than 2 and not more than a purification lots, wherein each of the purification lots comprises not less than 2 and not more than c purification batches, wherein a and c are independently an integer of 2 or higher, wherein b is an integer of not less than 2 and not more than a, wherein d is an integer of not less than 1 and not more than c−1, and wherein the d-th purification batch included in the b-th purification lot comprises:

mixing an oil layer obtained in the d+1-th purification batch of the b−1-th purification lot with the d-th silver salt aqueous solution of the b-th purification lot; and performing liquid separation on the mixed solution to obtain the d-th oil layer of the b-th purification lot and the d+1-th silver salt aqueous solution of the b-th purification lot.

In the above-described method, each purification batch does not necessarily have to follow the above-described rules, and for example, one or more purification batches may comprise different steps.

(Item B2)

The method according to item B1, wherein the c-th purification batch of the b-th purification lot comprises:

mixing raw material oils and fats with the c-th silver salt aqueous solution of the b-th purification lot; and performing liquid separation on the mixed solution to obtain the c-th oil layer of the b-th purification lot and the c+1-th silver salt aqueous solution of the b-th purification lot.

(Item B3)

The method according to item B1, further comprising:

performing organic solvent extraction on the silver salt aqueous solution obtained by performing liquid separation on the mixed solution, to obtain an extract comprising highly unsaturated fatty acids;

optionally, concentrating the extract obtained by the organic solvent extraction; and using precision distillation, molecular distillation, urea treatment method, silver nitrate treatment, fixed-bed chromatography, simulated moving-bed chromatography, or combinations of these, on the concentrate to allow the eicosapentaenoic acid (EPA) concentration to be 96.5% (w/w) or higher.

(Item B4)

The method according to item B3, wherein the arachidonic acid (AA) concentration is 1.0% (w/w) or lower.

(Item B5)

The method according to item B3, wherein the eicosatetraenoic acid (ETA) concentration is 1.0% (w/w) or lower.

Advantageous Effects of Invention

According to the production method of the present invention, unpurified highly unsaturated fatty acids and derivatives thereof can be industrially purified to pharmaceutical-grade products at a low cost.

DESCRIPTION OF EMBODIMENTS

Figure 1:
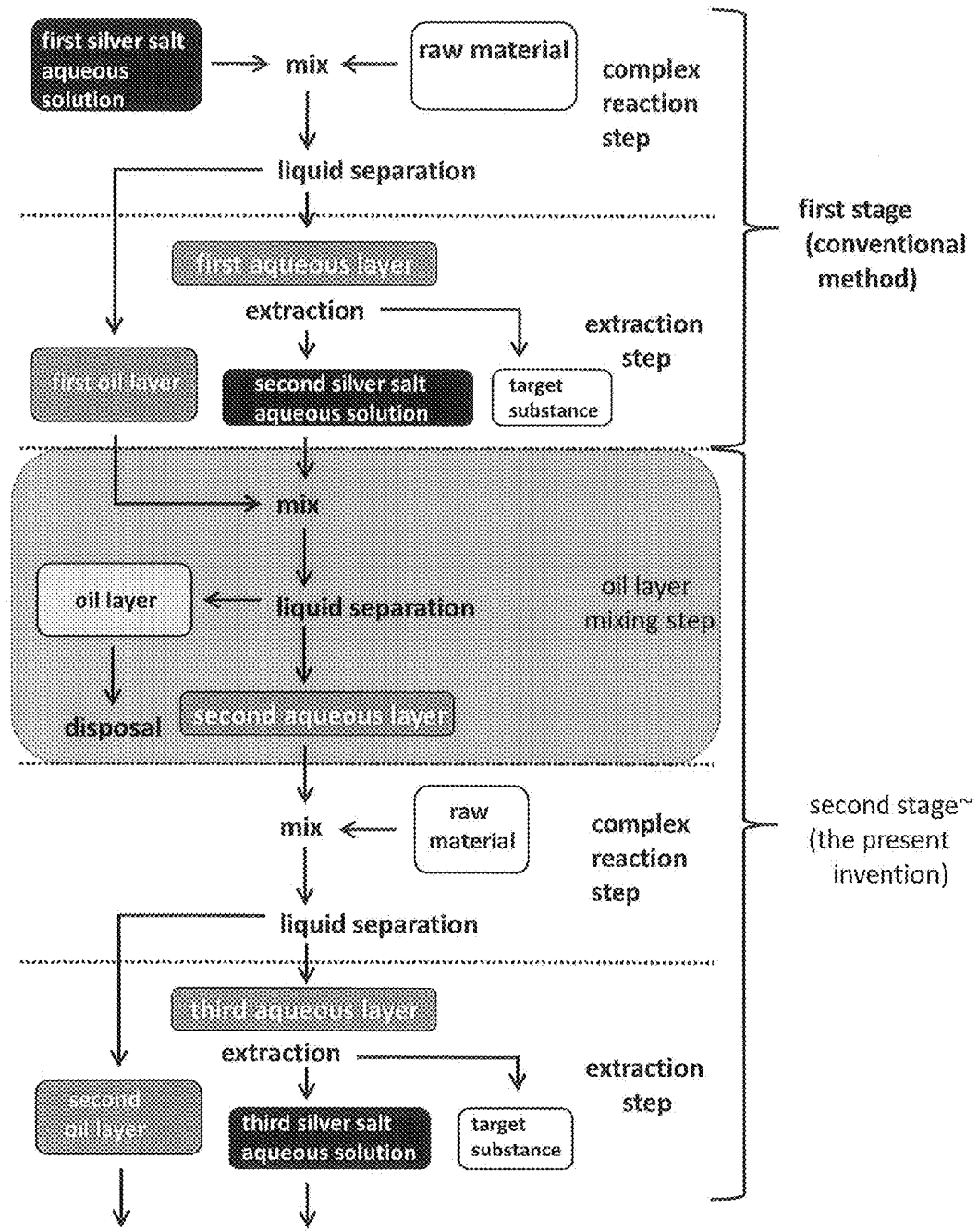
FIG. 1 schematically shows a first exemplary embodiment of the present invention.

Hereinafter, the present invention will be described. Throughout the present specification, it should be understood that unless particularly stated otherwise, an expression in its singular form also includes the conception of plurality. It should be also understood that unless particularly stated otherwise, the terms used in the present specification have the meanings that are conventionally used in the art. Therefore, unless defined otherwise, all technical and scientific terms used in the present specification have the same meanings as commonly understood by those having ordinary skill in the art to which the present invention pertains. In the case of conflict, the present specification, including the definitions, will control. In addition, in the present specification, "wt %" and "percent concentration of mass" can be interchangeably used. Furthermore, in the present specification, unless particularly stated otherwise, "%" means "wt %".

(Definition of Terms)

Hereinafter, the definitions of the terms that are particularly used in the present specification will be listed.

The term "raw material oils and fats" as used herein refers to oils and fats that are used as the raw materials in the purification of the present invention. Deacidification treatment may or may not be performed on the raw material oils and fats. Preferably, the raw material oils and fats of the present invention are raw material oils and fats on which deacidification treatment is performed.

The term "raw materials" as used herein refers to any substances including substances that are selected from the group consisting of highly unsaturated fatty acids and derivatives thereof. For example, the "raw materials" of the present invention can be, but are not limited to, the above-described "raw material oils and fats" and an "oil layer" generated in the purification process of the present invention. When the "oil layer" generated in the purification process of the present invention comprises substances that are selected from the group consisting of highly unsaturated fatty acids and derivatives thereof, they can be utilized as the raw materials of purification of the present invention without being disposed.

The term "purification" as used herein refers to any operation that increases the concentration of substances to be the target of purification.

The term "purification batch" as used herein refers to an operation of increasing the concentration of substances to be the target of purification in a silver salt aqueous solution. Thus, representatively, when a silver salt aqueous solution is subjected to the "purification batch", it is possible to obtain a silver salt aqueous solution having an increased concentration of the targeted substances. A plurality of (two or more) purification batches may be referred to as a "purification lot". Each purification lot does not necessarily have to comprise the same number of purification batches.

The term "highly unsaturated fatty acids" as used herein means unsaturated fatty acids having 16 or higher carbon number, which also have two or more double bonds within the molecule. For example, they can be, but are not limited to, docosahexaenoic acid (C22:6, DHA), eicosapentaenoic acid (C20:5, EPA), arachidonic acid (C20:4, AA), docosapentaenoic acid (C22:5, DPA), stearidonic acid (C18:4), linolenic acid (C18:3), and linoleic acid (C18:2). The derivatives of the highly unsaturated fatty acids that can be obtained with the acquisition method of the present invention refer to derivatives where fatty acids may or may not be the free type. For example, they can be, but are not limited to, highly unsaturated fatty acids, and ester-type derivatives such as methyl ester and ethyl ester, amide-type derivatives such as amide and methyl amide, fatty alcohol-type derivatives, triglyceride, diglyceride, and monoglyceride, of highly unsaturated fatty acids. Preferably, the target substances in the purification method of the present invention is ethyl esters selected from the group consisting of docosapentaenoic acid, eicosapentaenoic acid, docosahexaenoic acid, and ethyl esters of lower alcohols of those acids.

The term "silver salt" as used herein refers to silver salt that may form a complex with unsaturated bonds in unsaturated fatty acids. For example, it can be, but is not limited to, silver nitrate salt, silver perchlorate salt, silver acetate salt, silver trichloroacetate salt, and silver trifluoroacetate salt. The silver salt is dissolved into water such that the concentration becomes, preferably 15% or higher, more preferably 20% or higher, and even more preferably 40% or higher, to achieve a silver salt aqueous solution, and this is used for purification of highly unsaturated fatty acid derivatives. In addition, the silver salt concentration in the silver salt aqueous solution is not particularly limited, but preferably the saturating concentration is the upper limit.

The term "antioxidant" as used herein refers to a substance that reduces or removes harmful reactions involved with oxygen in living organisms, foods, daily necessities, and industrial raw materials. Representatively, the antioxidant can be, but is not limited to, butylhydroxytoluene, tocopherol, and a tocopherol derivative. For example, the tocopherol derivative can be, but is not limited to, d-α-tocopherol, d-β-tocopherol, d-γ-tocopherol, d-δ-tocopherol, l-α-tocopherol, l-β-tocopherol, l-γ-tocopherol, and l-δ-tocopherol; dl-α-tocopherol, dl-β-tocopherol, dl-γ-tocopherol, and dl-δ-tocopherol, which are mixtures thereof; and tocopherol acetate, tocopherol succinate, tocopherol phosphate, tocopherol aspartate, tocopherol glutamate, tocopherol palmitate, tocopherol nicotinate, tocopherol linoleate, and polyethoxylated tocopherol, which are derivatives thereof.

In the purification method of the present invention, the method of selectively separating highly unsaturated fatty acid derivatives from a mixture of derivatives of fatty acids is representatively performed by, but is not limited to: adding an aqueous solution of silver salt that may form a complex with unsaturated bonds into the above-described mixture of derivatives of fatty acids containing the highly unsaturated fatty acid derivatives; stirring preferably for 5 minutes to 4 hours, more preferably for 10 minutes to 2 hours to form the complex of water-soluble silver salt-highly unsaturated fatty acid derivatives; and selectively dissolving only the highly unsaturated fatty acid derivatives into a silver salt aqueous solution.

In addition, with regard to the reaction temperature of the above-described highly unsaturated fatty acid derivatives and the silver salt aqueous solution, the lower limit can be any temperature as long as the silver salt aqueous solution is a liquid, and the upper limit is 100° C. However, in consideration of the oxidative stability of the highly unsaturated fatty acid derivatives, the solubility of silver salt to water, the generation speed of the complex, and the like, the reaction temperature is preferably 10 to 30° C.

At the time of contacting the above-described highly unsaturated fatty acid derivatives with the silver salt aqueous solution, said contact is preferably performed under inert gas, e.g., nitrogen atmosphere, while blocking out light by considering the oxidative stability of the highly unsaturated fatty acid derivatives and the stability of silver salt. For example, by setting nitrogen atmosphere during production, incorporation of oxygen, which is the cause of oxidation, can be blocked, and it is also possible to suppress the increase of peroxide due to oxidation of raw materials. In addition, by blocking out the light, which promotes oxidation, it is possible to further suppress oxidation and suppress the increase of peroxide.

The method of dissociating the highly unsaturated fatty acid derivatives from the complex of the above-described highly unsaturated fatty acid derivatives and silver salt is not particularly limited, but it is for example, extraction by organic solvents, and a method of adding water to insolubilize the highly unsaturated fatty acid derivatives for separation.

(Complex Formation of Highly Unsaturated Fatty Acids and Derivatives Thereof in an Oil Layer, and a Silver Salt Aqueous Solution)

While not wishing to be bound by theory, the present invention is a method of production with a high yield/high purity by mixing highly unsaturated fatty acids and derivatives thereof, which are raw materials, with a solution where a complex is formed with highly unsaturated fatty acids and derivatives thereof in an oil layer. Hereinafter, characteristics thereof will be described.

(1: Regarding a Complex with a Silver Salt Aqueous Solution)

A silver salt aqueous solution ionizes in water, and a water-soluble complex is formed by mixture of highly unsaturated fatty acids having three or more double bonds in the molecule and silver ions at a low temperature. The ease of formation of a complex depends on the number of double bonds within the molecule, and generally, the complex formation ability becomes higher as the number of double bonds within the molecule increases. Such property is one factor allowing high purification by the present invention.

(2: Regarding Impurities in Silver Nitrate Treatment)

When aiming for highly-pure purification achieving pharmaceutical grades of highly unsaturated fatty acids such as eicosapentaenoic acid, docosapentaenoic acid, and docosahexaenoic acid having five or more double bonds within the molecule as target substances, arachidonic acid and eicosatetraenoic acid having four double bonds will be contained in a fraction purified with a silver nitrate treatment as impurities in view of the molecular structures. Since the physical properties such as boiling point and polarity of those molecules closely resemble those of the targeted substances, they become the causes of greatly reducing the yield at the time of removal with various purification methods. Thus, in order to obtain low-cost targeted substances of pharmaceutical grades, a method of removing substances that would become candidates of impurities by purification without decreasing the yield of the targeted substances is desired.

(3: Regarding Complex Formation with an Oil Layer)

In conventional methods, an excess amount of a silver salt aqueous solution was added from the viewpoint of yield. Thus, excess silver ions were generated, and a complex was also formed with arachidonic acid and eicosatetraenoic acid having four double bonds, which become impurities. This resulted in decrease of purity and eventually in decrease of yield.

In the present invention, purification of substances selected from the group consisting of highly unsaturated fatty acids and derivatives thereof with a high purity/high yield is enabled by forming a complex by mixing the highly unsaturated fatty acids and derivatives thereof in an oil layer with a silver salt aqueous solution once to consume excess silver ions, or limiting the amount of silver ions to be added, and collecting the highly unsaturated fatty acids and derivatives thereof in the oil layer.

(Each Step of the Present Invention)

For example, the present invention provides a purification method of substances selected from the group consisting of highly unsaturated fatty acids and derivatives thereof, wherein the method comprises the steps of:

(a) contacting and stirring first raw materials comprising said substances with a first silver salt aqueous solution to collect a first oil layer and a first aqueous layer;

(b) separating said first aqueous layer into a second silver salt aqueous solution and said substances; and (c) contacting and stirring an aqueous solution selected from the group consisting of the first silver salt aqueous solution and the second silver salt aqueous solution with the first oil layer, for separation into an oil layer and an aqueous layer to obtain a second aqueous layer comprising said substances. Any substances including substances selected from the group consisting of highly unsaturated fatty acids and derivatives thereof are used as the raw materials to be used in this method. The examples of the raw materials of the present invention can be, but are not limited to, the above-described raw material oils and fats, and the oil layer generated in the purification process of the present invention.

In this regard, the condition of the above-described contacting and stirring is not particularly limited, and thus well-known separation/purification methods using a silver salt aqueous solution (for example, Patent Literatures 1-4) can be used. For example, the concentration of the silver salt can be 1%, 3%, 5%, 10%, 15%, 20%, 30%, 40%, 50%, 60%, and a saturating concentration.

For the separation of the oil layer and the aqueous layer from the mixture made by contacting and stirring, a well-known method can be utilized. For example, standing or centrifugal separation can be used. For separation of highly unsaturated fatty acids and/or derivatives thereof (for example, highly unsaturated fatty acid ethyl esters) from the aqueous layer, a well-known method can be utilized. For example, n-heptane and the like can be used.

For the formation of a composite (complex) of silver salt and the highly unsaturated fatty acids and/or derivatives thereof, a well-known method can be used. For example, the method can be, but is not limited to, low temperatures. For the separation of the highly unsaturated fatty acids and/or derivatives thereof from the composite (complex), a well-known method can be used. For example, the method can be, but is not limited to, heating and solvent extraction.

(First Exemplary Embodiment of the Present Invention)

An embodiment of the present invention will be explained below by referring to FIG. 1.

A first silver salt aqueous solution is mixed with raw materials, and the mixed solution is separated into a first oil layer and a first aqueous layer. Highly unsaturated fatty acids and/or derivatives thereof, which are the target substances, are extracted from the first aqueous layer, and the remaining solution becomes a second silver salt aqueous solution. This second silver salt aqueous solution is mixed with the first oil layer, and the mixed solution is separated into an oil layer and a second aqueous layer. Since the oil layer comprises the targeted substances only at a low concentration, it is disposed. Next, the second aqueous layer may be subjected to further purification in the same manner as the mixed solution of the first silver salt aqueous solution and the raw materials.

(Second Exemplary Embodiment of the Present Invention)

Figure 2:
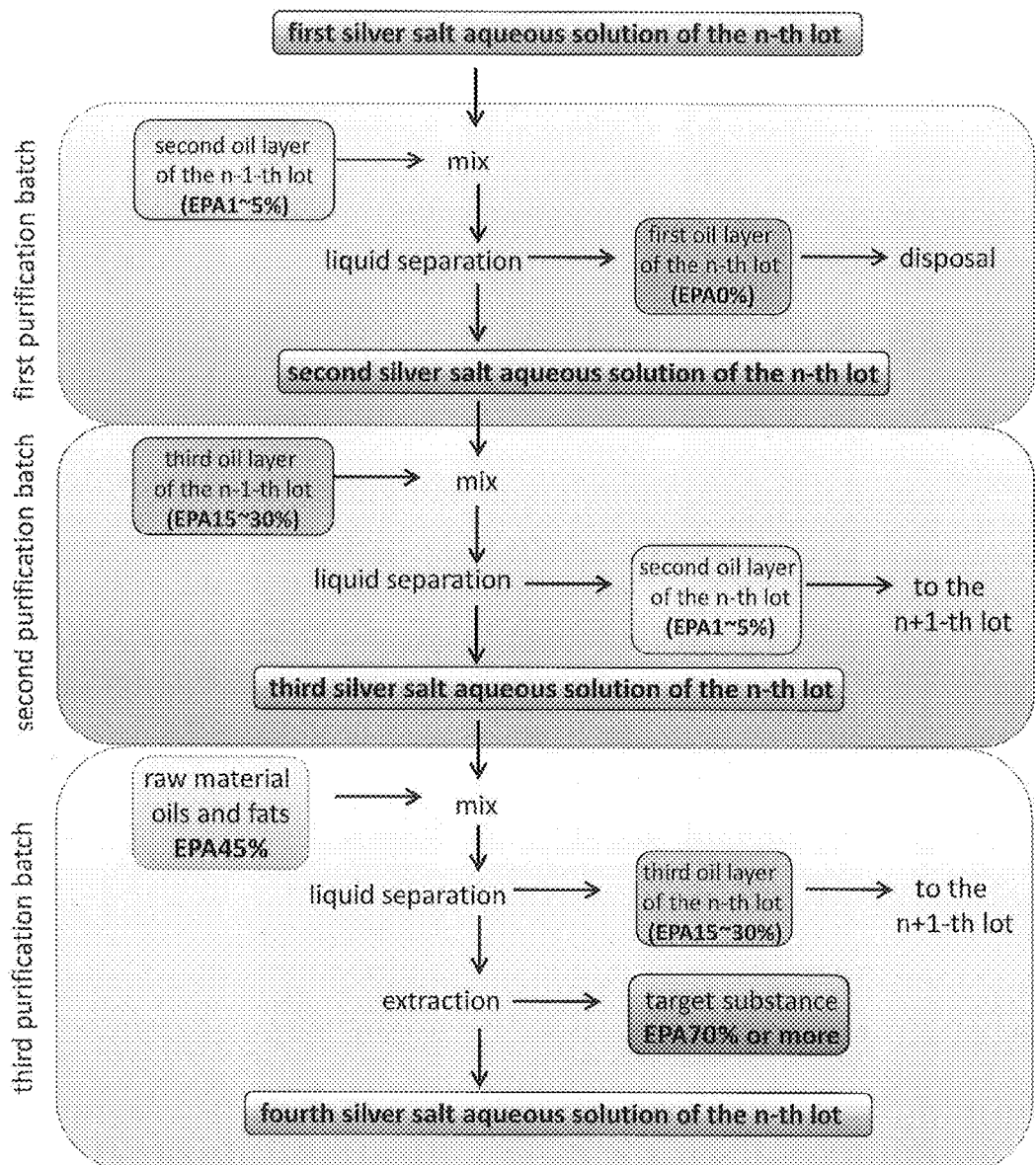
FIG. 2 schematically shows a second exemplary embodiment ("n"-th purification lot comprising three purification batches) of the present invention.
Figure 3:
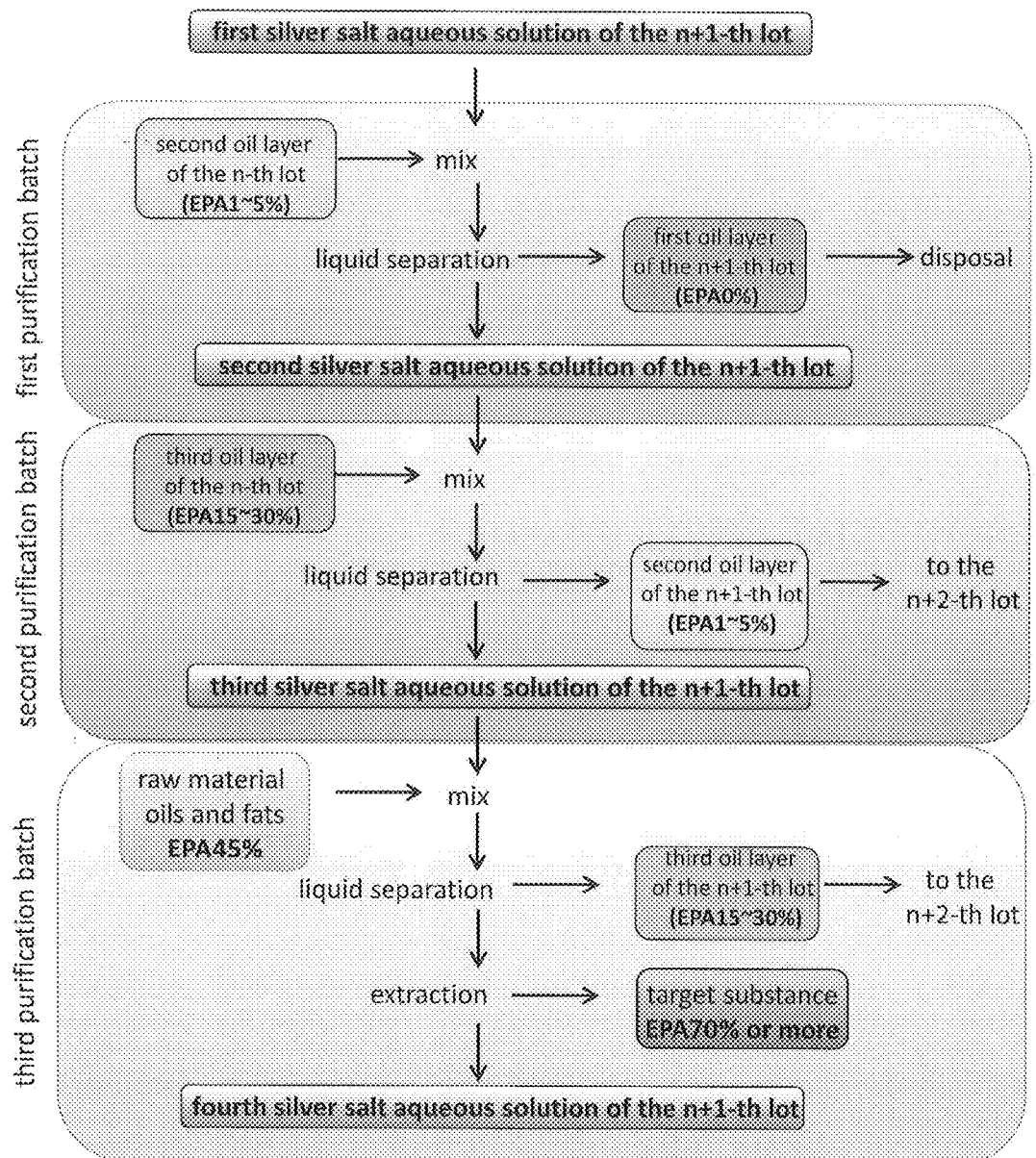
FIG. 3 schematically shows the second exemplary embodiment ("n+1"-th purification lot comprising three purification batches) of the present invention.
Figure 4:
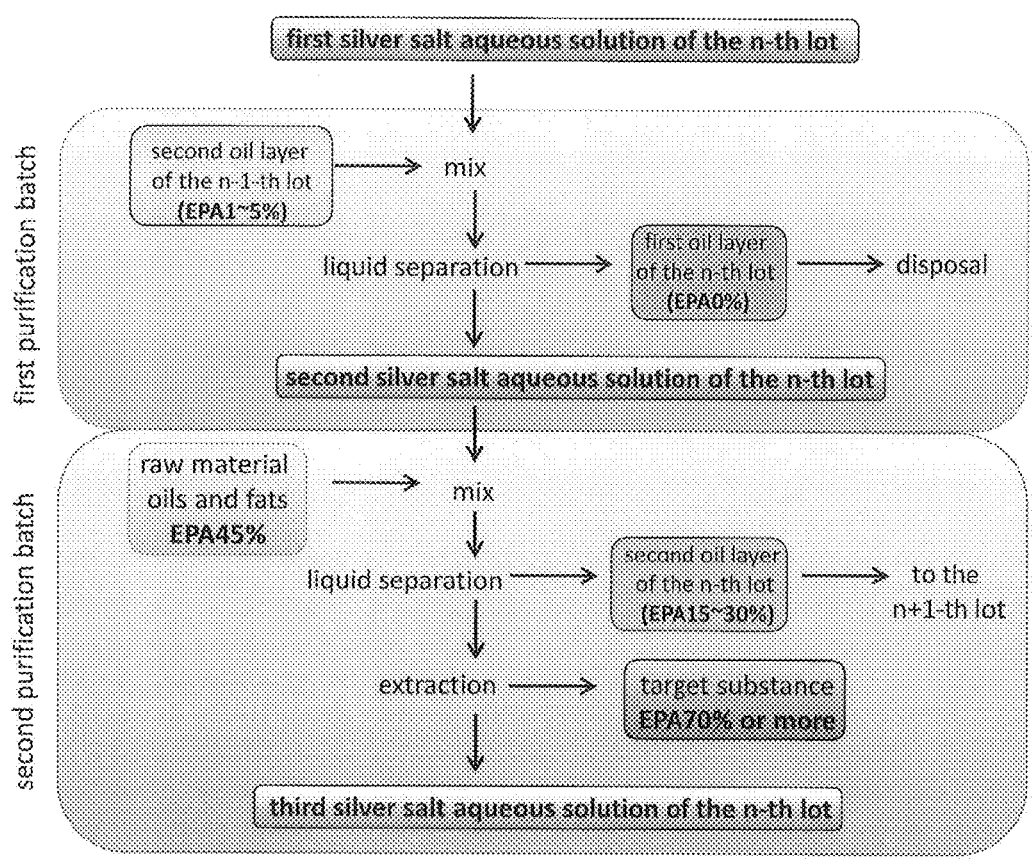
FIG. 4 schematically shows the second exemplary embodiment ("n"-th purification lot comprising two purification batches) of the present invention.

An embodiment of the present invention that reuses an oil layer obtained in the purification step as a raw material without disposing the oily layer, will be explained by referring to FIGS. 2-4.

A unit where two or more purification batches are combined is set as a purification lot, and by continuously performing a plurality of purification lots, it is possible to continuously purify highly unsaturated fatty acids and/or derivatives thereof. FIG. 2 schematically shows a "n"-th lot comprising three purification batches. Although a representative EPA concentration of each solution (oil layer, raw material oils and fats) is described, this concentration is only a rough indication. In each of the purification batches, an oil layer or raw material oils and fats is mixed with a silver salt aqueous solution, and an oil layer and a silver salt aqueous solution are prepared by liquid separation. The obtained silver salt aqueous solution is either used to be mixed with the oil layer or raw material oils and fats in the next purification batch of the same lot, or when said purification batch is the final purification batch in said lot, is used to be mixed with the oil layer in the first purification batch of the next lot. For example, when the purification lot comprises three purification batches, the fourth silver salt aqueous solution of the n-th lot prepared in the third purification batch of the n-th lot will be used as the first silver salt aqueous solution in the n+1-th lot (i.e., the next lot) to be mixed with an oil layer in the first purification batch in the n+1-th lot. The first oil layer prepared in the first purification batch representatively has a low EPA concentration, and thus it is disposed. However, when the EPA concentration is high, the first oil layer can be reused as a purification raw material without being disposed.

Subsequently to the n-th purification lot schematically shown in FIG. 2, the n+1-th lot schematically shown in FIG. 3 can be performed. An oil layer to be used in the first purification batch of the n+1-th lot is representatively "the second oil layer of the n-th lot" derived from the previous lot. An oil layer to be used in the second purification batch of the n+1-th lot is representatively "the third oil layer of the n-th lot" derived from the previous lot.

Each purification lot is not necessarily required to comprise three purification batches, and it can comprise any number of purification batches of two or more. FIG. 4 schematically shows a purification lot comprising two purification batches. When the purification lot comprises two purification batches, the third silver salt aqueous solution of the n-th lot obtained in the second purification batch can be used as the first silver salt aqueous solution in the n+1-th lot.

(Purified Product that can be Obtained by the Present Invention)

The purity of eicosapentaenoic acid (EPA) that can be obtained by the present invention is, for example, 90% (w/w) or higher, 61% (w/w) or higher, 62% (w/w) or higher, 63% (w/w) or higher, 64% (w/w) or higher, 65% (w/w) or higher, 66% (w/w) or higher, 67% (w/w) or higher, 68% (w/w) or higher, 69% (w/w) or higher, or 70% (w/w) or higher. The purity of EPA in the starting material to be used for the preparation of EPA having these purities is representatively, but not limited to, 40 (w/w) %.

The purity of eicosapentaenoic acid (EPA) obtained by the present invention can be further increased by using a well-known method (for example, precision distillation, molecular distillation, urea treatment method, silver nitrate treatment, fixed-bed chromatography, simulated moving-bed chromatography, or combinations of these), and the purity of eicosapentaenoic acid (EPA) that can be obtained as a result of such further purification is, for example, 90% (w/w) or higher, 91% (w/w) or higher, 92% (w/w) or higher, 93% (w/w) or higher, 94% (w/w) or higher, 95% (w/w) or higher, 96% (w/w) or higher, 96.5% (w/w) or higher, 97% (w/w) or higher, or 97.5% (w/w) or higher.

The concentration of arachidonic acid (AA) in the composition comprising eicosapentaenoic acid (EPA) obtained by the present invention is 0.4% (w/w) or lower, 0.8% (w/w) or lower, 1.0% (w/w) or lower, 1.5% (w/w) or lower, or 3.0% (w/w) or lower. The concentration of eicosatetraenoic acid (ETA) in the composition comprising eicosapentaenoic acid (EPA) obtained by the present invention is 0.4% (w/w) or lower, 0.8% (w/w) or lower, 1.0% (w/w) or lower, 1.5% (w/w) or lower, or 3.0% (w/w) or lower.

Hereinafter, the purification method of highly unsaturated fatty acid derivatives of the present invention will be specifically explained based on the Examples and the like. However, the present invention is not limited thereto.

EXAMPLES

Hereinafter, the present invention will be explained more specifically concerning purification of eicosapentaenoic acid based on the Examples and the Comparative examples. However, the present invention is not limited to the Examples below.

Systems using conventional methods will be described as comparative examples. In Example 1, a test was conducted by using an oil layer created as a by-product from Comparative example 1.

Comparative Example 1

The test conditions were as below.
Starting raw materials: EPA ethyl ester 40%-containing oils and fats
Silver nitrate aqueous solution concentration: 50%
Collection solvent: n-heptane
Raw material usage: 20 g
Silver nitrate aqueous solution usage: 100 g
Collection solvent usage: 200 g
Reaction Conditions:
1. Raw materials and a silver nitrate aqueous solution were mixed, and after stirring for three hours at 10° C., a lower layer (aqueous layer) and an upper layer (oil layer 1) were collected.
2. 200 g of n-heptane was added to the lower layer, and after heating for two hours at 80° C., an upper layer (oil layer 2) was collected.
3. After vacuum concentration, the yield was evaluated from the obtained amount, and the purity was evaluated from GC (Shimadzu 2010 plus) analysis.

Example 1

Test Conditions
Raw materials: EPA ethyl ester 40%-containing oils and fats
Silver nitrate aqueous solution concentration: 50%
Collection solvent: n-heptane
Raw material usage: 20 g
Silver nitrate aqueous solution usage: 100 g
Collection solvent usage: 200 g
Reaction Conditions:
1. A silver nitrate aqueous solution was added to the upper layer (oil layer 1) collected in Comparative Example 1, and after stirring for three hours at 10° C., a lower layer (aqueous layer) was collected.
2. Raw materials were added to the collected lower layer, and after stirring for three hours at 10° C., a lower layer (aqueous layer) was collected.
3. 100 g of n-heptane was added to the lower layer, and after heating for two hours at 80° C., an upper layer (oil layer 2) was collected.
4. After vacuum concentration, the yield was evaluated from the obtained amount, and the purity was evaluated from GC (Shimadzu 2010 plus) analysis.

The results of Comparative example 1 and Example 1 will be described in the tables below.

Table 1: Fatty Acid Composition of the Purified Products of Comparative Example 1 and Example 1

TABLE 1

| | Fatty acid composition (area %) | | |
|---|---|---|---|
| | Raw material | Comparative example 1 | Example 1 |
| Arachidonic acid | 2.4 | 1.6 | 1.2 |
| Eicosatetraenoic acid | 1.7 | 1.5 | 0.7 |
| Eicosapentaenoic acid | 48.4 | 78.2 | 82.4 |
| Docosahexaenoic acid | 7.0 | 12.2 | 11.9 |

Table 2: Yields of the Purified Products of Comparative Example 1 and Example 1

TABLE 2

| | Comparative example 1 | Example 1 |
|---|---|---|
| Ester yield (%) | 42.5 | 55.4 |

From the above results, due to effective utilization of oil layers, the purities of impurities that are difficult to be removed such as arachidonic acid and eicosatetraenoic acid were reduced as compared to the conventional methods, while the purity of eicosapentaenoic acid was improved as compared to the conventional methods.

In addition, by collecting eicosapentaenoic acid in oil layers, the yield was successfully improved by over 10 points as compared to the conventional methods.

Thus, it was demonstrated that eicosapentaenoic acid can be produced with a high purity/high yield at a low cost as compared to the conventional methods.

Example 2

The test conditions were as below.
Firstly, 50 g of distilled water was added to 50 g of silver nitrate to be stirred/dissolved, as a first batch. 20 g of a mixture of fatty acid ethyl esters (EPA ethyl ester 40.4% (fatty acid composition area %), DHA ethyl ester purity 15.0%) was added to 100 g of this 50% silver nitrate aqueous solution, and stirring was performed for three hours at 10° C. Subsequently, the solution was left to stand for 1 hour, and was separated into two layers. This upper layer (oil layer) was stored, and the lower layer (aqueous layer) was separately collected for addition of 100 g of n-heptane to be stirred for 2 hours at 80° C. Subsequently, the solution was left to stand for 1 hour, and was separated into two layers. This upper layer was separately collected to obtain a concentrate of highly unsaturated fatty acid ethyl esters. In addition, the lower layer containing silver nitrate and the stored oil layer were further used for purification of highly unsaturated fatty acid ethyl esters in the subsequent batches.

In the second batch and onwards, the operations described below were repeatedly conducted. The lower layer containing silver nitrate was mixed with the stored oil layer, and was stirred for three hours at 10° C. A lower layer (aqueous layer) was separately collected, and mixed with 20 g of a mixture of fatty acid ethyl esters to be stirred for three hours at 10° C. Subsequently, the solution was left to stand for 1 hour, and was separated into two layers. This upper layer (oil layer) was stored, and the lower layer (aqueous layer) was separately collected for addition of 100 g of n-heptane to be stirred for 2 hours at 80° C. Subsequently, the solution was left to stand for 1 hour, and was separated into two layers. This upper layer was separately collected to obtain a concentrate of highly unsaturated fatty acid ethyl esters. The above-described reactions were carried out under nitrogen atmosphere. The results of repeating these operations and treating the above-described mixture up to five batches will be shown in Table 3.

Table 3: Result List of the Examples

TABLE 3

|  |  | Raw material | First batch (conventional method) | Second batch | Third batch | Fourth batch | Fifth batch |
| --- | --- | --- | --- | --- | --- | --- | --- |
| Fatty acid composition (area %) | Arachidonic acid | 3.6 | 2.4 | 1.7 | 1.8 | 1.7 | 1.7 |
|  | Eicosatetraenoic acid | 2.5 | 1.9 | 1.4 | 1.4 | 1.5 | 1.4 |
|  | Eicosapentaenoic acid | 40.4 | 60.9 | 65.2 | 65.3 | 65.3 | 65.3 |
|  | Docosahexaenoic acid | 15.0 | 26.4 | 25.7 | 25.9 | 29.7 | 25.4 |
| Ester yield (%) |  | — | 42.5 | 55.4 | 54.2 | 59.0 | 55.1 |

It can be understood that the results similar to those of Example 1 are stably reproduced even by repeating the treatments. From these results, it is demonstrated that eicosapentaenoic acid can be produced with a high purity/high yield at a low cost as compared to the conventional methods.

Next, in order to judge the effects of the present invention more clearly, the results of repeatedly carrying out the conventional methods will be described below as Comparative example 2.

Comparative Example 2

The test conditions were as below.
Starting raw materials: EPA ethyl ester 40%-containing oils and fats Silver nitrate aqueous solution concentration: 50%
Collection solvent: n-heptane
Raw material usage: 20 g
Silver nitrate aqueous solution usage: 100 g
Collection solvent usage: 200 g
Reaction Conditions:

1. The raw materials and a silver nitrate aqueous solution were mixed, and after stirring for three hours at 10° C., a lower layer (aqueous layer) and an upper layer (oil layer 1) were collected.
2. 200 g of n-heptane was added to the lower layer, and after heating for two hours at 80° C., an upper layer (oil layer 2) was collected.
3. After vacuum concentration, the yield was evaluated from the obtained amount, and the purity was evaluated from GC (Shimadzu 2010 plus) analysis.
4. The above operations were carried out for five batches.

The results of Comparative example 2 will be described in the table below.

Table 4: Fatty Acid Composition and Yields of the Purified Products of Five Batches Carried Out in Comparative Example 2

TABLE 4

|  |  | Raw material | First batch | Second batch | Third batch | Fourth batch | Fifth batch |
| --- | --- | --- | --- | --- | --- | --- | --- |
| Fatty acid composition (area %) | Arachidonic acid | 3.6 | 2.6 | 2.5 | 2.5 | 2.5 | 2.6 |
|  | Eicosatetraenoic acid | 2.6 | 2.0 | 2.0 | 1.9 | 1.9 | 1.9 |
|  | Eicosabentaenoic acid | 41.0 | 61.1 | 61.3 | 61.1 | 60.8 | 60.7 |
|  | Docosahexaenoic acid | 15.2 | 24.8 | 24.6 | 24.7 | 24.5 | 24.6 |
| Ester yield (%) |  | — | 42.2 | 42.1 | 42.2 | 42.7 | 42.6 |

Results similar to those of Comparative example 1 were continuously obtained. When compared to the results of Example 2, it was possible to confirm improvement of quality and improvement of yields associated with reduction of arachidonic acid (AA) and eicosatetraenoic acid (ETA) contents as asserted by the present invention.

Example 3

Next, with regard to the case of re-using the oil layer for a plurality of times, Example 3 describes results of re-using the oil layer for two times.

Results will be shown regarding a system where the stored oil layer is mixed with a lower layer containing silver nitrate to be stirred for three hours at 10° C., and eicosapentaenoic acid is also collected from an upper layer (oil layer) created as a by-product in the step of separately collecting a lower layer (aqueous layer).

The test conditions were as below.

As the first batch, 50 g of distilled water was added to 50 g of silver nitrate for stirring/dissolving. 20 g of a mixture of fatty acid ethyl esters (EPA ethyl ester 40.4% (fatty acid composition area %), DHA ethyl ester purity 15.0%) was added to 100 g of 50% silver nitrate aqueous solution, and the solution was stirred for three hours at 10° C. Subsequently, the solution was left to stand for 1 hour, and was separated into two layers. This upper layer (oil layer) was stored, and the lower layer (aqueous layer) was separately collected for addition of 100 g of n-heptane to be stirred for two hours at 80° C. Subsequently, the solution was left to stand for 1 hour, and was separated into two layers. This upper layer was separately collected to obtain a concentrate of highly unsaturated fatty acid ethyl esters. In addition, the lower layer containing silver nitrate and the stored oil layer as an oil layer 2 were further used for purification of highly unsaturated fatty acid ethyl esters in the subsequent batches.

As the second batch, the stored oil layer 1 was mixed with the lower layer containing silver nitrate, and was stirred for three hours at 10° C. At the time of separately collecting the lower layer (aqueous layer), the upper layer (oil layer) was stored to be used in purification of highly unsaturated fatty acid ethyl esters in the subsequent batches as the oil layer 2. The separately collected lower layer (aqueous layer) was mixed with 20 g of a mixture of fatty acid ethyl esters, and was stirred for three hours at 10° C. Subsequently, the solution was left to stand for 1 hour, and was separated into two layers. This upper layer (oil layer) was stored, and the lower layer (aqueous layer) was separately collected for addition of 100 g of n-heptane to be stirred for two hours at 80° C. Subsequently, the solution was left to stand for 1 hour, and was separated into two layers. This upper layer was separately collected to obtain a concentrate of highly unsaturated fatty acid ethyl esters.

In the third batch and onwards, the operations described below were repeatedly carried out. The stored oil layer 2 was mixed with the lower layer containing silver nitrate, and was stirred for three hours at 10° C. The lower layer (aqueous layer) was separately collected, and was mixed with the stored oil layer 1 to be stirred for three hours at 10° C. This upper layer (oil layer) was stored, and the lower layer (aqueous layer) was separately collected and mixed with 20 g of a mixture of fatty acid ethyl esters to be stirred for three hours at 10° C. Subsequently, the solution was left to stand for 1 hour, and was separated into two layers. This upper layer (oil layer) was stored, and the lower layer (aqueous layer) was separately collected for addition of 100 g of n-heptane to be stirred for two hours at 80° C. Subsequently, the solution was left to stand for 1 hour, and was separated into two layers. This upper layer was separately collected to obtain a concentrate of highly unsaturated fatty acid ethyl esters.

The above-described reactions were carried out under nitrogen atmosphere. The results of repeating these operations and treating the above-described mixture up to five batches will be shown in Table 5.

Table 5: Result List of the Examples

TABLE 5

| | | Raw material | First batch (conventional method) | Second batch | Third batch | Fourth batch | Fifth batch |
|---|---|---|---|---|---|---|---|
| Fatty acid composition (area %) | Arachidonic acid | 3.5 | 2.6 | 1.7 | 2.0 | 1.9 | 2.0 |
| | Eicosatetraenoic acid | 2.0 | 1.8 | 1.4 | 1.6 | 1.6 | 1.6 |
| | Eicosapentaenoic acid | 42.3 | 60.5 | 65.2 | 70.2 | 70.5 | 70.2 |
| | Docosahexaenoic acid | 17.4 | 28.0 | 27.7 | 26.3 | 26.7 | 26.2 |
| Ester yield (%) | | — | 43.3 | 52.2 | 56.5 | 56.4 | 56.1 |

In the second batch and onwards, the purity and the yield of eicosapentaenoic acid are further stably and continuously improved as compared to Example 2. Although this process is more complicated than Example 2 as a production process, the results of Example 3 are more desirable for products where the cost of raw materials account for the majority of the production cost as in the present case.

INDUSTRIAL APPLICABILITY

According to the production method of the present invention, pharmaceutical-grade products of highly unsaturated fatty acids and/or derivatives thereof can be industrially purified at a low cost from unpurified highly unsaturated fatty acids and derivatives thereof.

The invention claimed is:
1. A purification method of substances selected from the group consisting of highly unsaturated fatty acids and derivatives thereof, comprising:
   (a) contacting and stirring first raw materials comprising the substances with a first silver salt aqueous solution to collect a first oil layer and a first aqueous layer;
   (b) separating the first aqueous layer into a second silver salt aqueous solution and the substances;
   (c) contacting and stirring an aqueous solution selected from the group consisting of the first silver salt aqueous solution and the second silver salt aqueous solution with the first oil layer, for separation into an oil layer and an aqueous layer to obtain a second aqueous layer comprising the substances; and
   (d) contacting and stirring the second aqueous layer with second raw materials comprising the substances to collect a second oil layer and a third aqueous layer, wherein the second oil layer comprises the substances, and wherein the derivatives of said highly unsaturated fatty acids are selected from any one of methyl ester, ethyl ester, amide, methyl amide, triglyceride, diglyceride, or monoglyceride derivatives.
2. The method of claim 1, further comprising separating the third aqueous layer into a third silver salt aqueous solution and the substances.

3. The method of claim 1, further comprising
isolating the substances from the second oil layer.

4. The method of claim 2, further comprising
contacting and stirring a silver salt aqueous solution selected from the first silver salt aqueous solution, the second silver salt aqueous solution, and the third silver salt aqueous solution with the second oil layer, for separation into an oil layer and an aqueous layer to obtain a fourth aqueous layer comprising the substances.

5. The method according to claim 1, wherein the highly unsaturated fatty acid derivatives are highly unsaturated fatty acid ethyl esters, and wherein the highly unsaturated fatty acid ethyl esters are selected from the group consisting of docosapentaenoic acid, eicosapentaenoic acid, docosahexaenoic acid, and ethyl esters of lower alcohols of those, having five or more double bonds within the molecule.

6. A purification method of substances selected from the group consisting of highly unsaturated fatty acids and derivatives thereof, comprising:
contacting and stirring a first oil layer, which is collected by contacting and stirring first raw materials comprising the substances with a first silver salt aqueous solution, with a second silver salt aqueous solution obtained by separating a first aqueous layer, which is collected by contacting and stirring the first raw materials comprising the substances with the first silver salt aqueous solution, into the second silver salt aqueous solution and the substances, for separation into an oil layer and an aqueous layer to collect a second aqueous layer comprising the substances, contacting and stirring the second aqueous layer with second raw materials comprising the substances to collect a second oil layer and a third aqueous layer, wherein the second oil layer comprises the substances; or
contacting and stirring a first oil layer, which is collected by contacting and stirring first raw materials comprising the substances with a first silver salt aqueous solution, with the first silver salt aqueous solution, for separation into an oil layer and an aqueous layer to collect a second aqueous layer comprising the substances, contacting and stirring the second aqueous layer with second raw materials comprising the substances to collect a second oil layer and a third aqueous layer, wherein the second oil layer comprises the substances,
wherein the derivatives of said highly unsaturated fatty acids are selected from any one of methyl ester, ethyl ester, amide, methyl amide, triglyceride, diglyceride or monoglyceride derivatives.

7. The method of claim 6, further comprising
separating the third aqueous layer into a third silver salt aqueous solution and the substances.

8. The method according to claim 6, further comprising
isolating the substances from the second oil layer.

9. The method according to claim 7, further comprising
contacting and stirring a silver salt aqueous solution selected from the group consisting of the first silver salt aqueous solution, the second silver salt aqueous solution, and the third silver salt aqueous solution with the second oil layer, for separation into an oil layer and an aqueous layer to obtain a fourth aqueous layer comprising the substances.

10. The method according to claim 6, wherein the highly unsaturated fatty acid derivatives are highly unsaturated fatty acid ethyl esters, and wherein the highly unsaturated fatty acid ethyl esters are selected from the group consisting of docosapentaenoic acid, eicosapentaenoic acid, docosahexaenoic acid, and ethyl esters of lower alcohols of those, having five or more double bonds within the molecule.

11. A purification method of substances selected from the group consisting of highly unsaturated fatty acids and derivatives thereof, the method comprising not less than 2 and not more than (a) purification lots, wherein each of the purification lots comprises not less than 2 and not more than (c) purification batches, wherein (a) and (c) are independently an integer of 2 or higher, wherein (b) is an integer of not less than 2 and not more than (a), wherein (d) is an integer of not less than 1 and not more than (c−1), and wherein a $(d^{th})$ purification batch included in a $(b^{th})$ purification lot comprises:
mixing an oil layer obtained in a $(d+1^{th})$ purification batch of a $(b-1^{th})$ purification lot with a $(d^{th})$ silver salt aqueous solution of the $(b^{th})$ purification lot;
performing liquid separation on the mixed solution to obtain a $(d^{th})$ oil layer of the $(b^{th})$ purification lot and a $(d+1^{th})$ silver salt aqueous solution of the $(b\text{-}^{th})$ purification lot; and
mixing raw material oils and fats with a $(c^{th})$ silver salt aqueous solution of the $(b^{th})$ purification lot;
wherein the derivatives of said highly unsaturated fatty acids are selected from any one of methyl ester, ethyl ester, amide, methyl amide triglyceride, diglyceride or monoglyceride derivatives.

12. The method of claim 11, wherein a $(c^{th})$ purification batch of the $(b^{th})$ purification lot further comprises:
performing liquid separation on the mixed solution to obtain a $(c^{th})$ oil layer of the $(b^{th})$ purification lot and a $(c+1^{th})$ silver salt aqueous solution of the $(b\text{-}^{th})$ purification lot.

13. The method of claim 11, further comprising:
performing organic solvent extraction on the $(d+1^{th})$ silver salt aqueous solution obtained by performing liquid separation on the mixed solution, to obtain an extract comprising highly unsaturated fatty acids;
optionally, concentrating the extract obtained by the organic solvent extraction; and
using precision distillation, molecular distillation, urea treatment method, silver nitrate treatment, fixed-bed chromatography, simulated moving-bed chromatography, or combinations of these, on the concentrate to allow an eicosapentaenoic acid (EPA) concentration to be 96.5% (w/w) or higher.

14. The method of claim 13, wherein an arachidonic acid (AA) concentration is 1.0% (w/w) or lower.

15. The method of claim 13, wherein an eicosatetraenoic acid (ETA) concentration is 1.0% (w/w) or lower.

* * * * *

UNITED STATES PATENT AND TRADEMARK OFFICE
CERTIFICATE OF CORRECTION

PATENT NO. : 10,196,584 B2
APPLICATION NO. : 15/577294
DATED : February 5, 2019
INVENTOR(S) : Hiroshi Tabata Page 1 of 1

It is certified that error appears in the above-identified patent and that said Letters Patent is hereby corrected as shown below:

In the Claims

Column 20, Claim 11, Line 19:
"not less than 2and not more than (a), wherein (d) is an" should read, --not less than 2 and not more than (a), wherein (d) is an--.

Column 20, Claim 11, Line 34:
"ester, amide, methyl amide triglyceride, diglyceride or" should read, --ester, amide, methyl amide, triglyceride, diglyceride or--.

Signed and Sealed this
First Day of September, 2020

Andrei Iancu
*Director of the United States Patent and Trademark Office*